United States Patent [19]
Wakabayashi et al.

[11] Patent Number: 5,263,373
[45] Date of Patent: Nov. 23, 1993

[54] MATERIAL TESTING MACHINE WITH SCREW COLUMNS MADE EXPANDABLE

[75] Inventors: Noboru Wakabayashi; Hisanori Fuse, both of Kyoto, Japan

[73] Assignee: Shimadzu Corporation, Kyoto, Japan

[21] Appl. No.: 856,674

[22] Filed: Mar. 24, 1992

[30] Foreign Application Priority Data

Mar. 29, 1991 [JP] Japan ................................. 3-091745

[51] Int. Cl.⁵ .............................................. G01N 3/08
[52] U.S. Cl. ........................................ 73/788; 254/98
[58] Field of Search ................. 73/788, 796, 818, 817, 73/834; 254/98; 100/230

[56] References Cited

U.S. PATENT DOCUMENTS 1,208,748 12/1916 Chew .................................. 73/826 X
2,352,600 7/1944 Brackett .................................. 254/98

Primary Examiner—Jerry W. Myracle
Attorney, Agent, or Firm—Nikaido, Marmelstein, Murray & Oram

[57] ABSTRACT

A material testing machine devised so as to be capable of complying with a long test piece without employing a long-sized screw columns. The machine consists essentially of a pair of intermediate rods rotatably installed on a table for being driven by a motor, a pair of screw columns screw-cut in the region corresponding to a possible elongation of a test piece and devised so as to be expandable with respect to and rotatable integrally with the pair of intermediate rods, holder means for rotatably holding the screw columns at any desired position of expansion, and a crosshead having both its ends screw-engaged with the pair of screw columns for being driven through the rotation of the screw columns to exert force on a test piece between the same and the table.

3 Claims, 4 Drawing Sheets

MATERIAL TESTING MACHINE WITH SCREW COLUMNS MADE EXPANDABLE

BACKGROUND OF THE INVENTION

The present invention relates to a material testing machine devised so as to make a test piece imposed with a test load with a crosshead driven by means of rotating screw columns A conventional material testing machine of this kind is exemplified by FIGS. 4 and 5, which respectively show an entire frontal outlined view of the machine and a partial detailed view illustrating the construction of the left half portion of the machine. The right half of the machine, though not shown, has a symmetrically similar construction.

A pair of supporting columns 1 (FIG. 5) vertically kept on the floor holds at the lower portion both ends of a table 2 (base rack) and supports at the upper portion a crossyoke 3 horizontally. On the table is installed a pair of right and left screw columns 4, by which a crosshead has both its ends supported through a pair of corresponding screw nuts (not shown). Each of the screw columns 4 has its lower end connected with a reduction gear 6 driven by a not shown motor through a rotation shaft 7.

The upper side of the table 2 and the lower side of the crosshead 5 are respectively provided with facing clutches (not shown) forming a pair of material gripping tools. Rotation of the motor in a predetermined direction, with a test piece gripped on both the ends by the clutches, makes each of the screw columns 4 to rotate through the rotation shaft 7 and the reduction gear 6, causing the crosshead 7 screw-engaged with the screw columns 4 to rise upward. The upper clutch fixed to the crosshead 5 is then lifted up to exert a tensile force to the test piece. Further, a reference numeral 8 in FIGS. 4 and 5 stands for a cover protecting the supporting columns 1 and the screw columns 4.

In such a general constitution of the machine, a longer test piece necessitates, as a matter of course, a larger distance between the crosshead 5 and the table 2. This requirement has conventionally been coped with replacement of the screw columns 4 with longer ones, whose cost is generally increased with an increase in length. However, if the elongation due to a tensile force is small, even a long test piece caused the stroke of the crosshead in operation to ramain short. This means that only a short region of the long screw columns is used in practice. Therefore, it is uneconomical to use expensive long-sized screw columns.

OBJECT AND SUMMARY OF THE INVENTION

The object of the present inventiom is to provide an improved material testing machine capable of testing a long test piece without using long-sized screw columns.

The present invention is briefed below by reference to an embodiment shwown in FIG. 1. A material testing machine with screw columns made expandable according to the present invention, as is understood from FIG. 1 illustrating the main part of the later detailed embodiment of the present invention, consists essentially of a pair of motor-driven intermediate rods 25 held vertical to the table 2; a pair of screw columns 21 provided with screws in a predetermined region covering a possible elongation of a test piece and mounted so as to be expandable with respect to and co-rotatable with the pair of intermediate rods 25; holder means 22 U and 22 L for rotatably holding the screw columns 21 at any desired position of expansion; and a crosshead 5 having both its ends screw-engaged with the pair of screw column 21 so as to be moved by the rotation of the screw columns to make a test piece loaded with a force between the crosshead 5 and the table 2.

In the above fundamental constitution of the machine, after the distance between the table 2 and the crosshead 5 is adjusted so as to correspond to the length of a test piece by expanding or contracting the screw columns 21 with respect to the intermediate rods 25, the screw columns 21 is fixed at an expanded or contracted position by means of the holder means 22U and 22L. When a long test piece is to be tested, for instance, the above mentioned distance between the table and the crosshead is made long by expanding the screw columns 21. Then the test piece is set between the table 2 and the crosshead 5, and the intermediate rods 25 are rotated in a predetermined direction by means of the motor. The rotation of the rods 25 causes the screw columns 21 to rotate therewith, resulting in the drive of the crosshead 5 exerting a force on the test piece.

Acoording to the present invention the screw columns with which the crosshead is screw-engaged are made not only expandable with respect to the intermediate rods (driven by the motor) but also ratatable in one body with those intermediate rods, and the screw columns can be fixed at any desired position of expansion or contraction. Accordingly, the present invention makes it possible to test a long size test piece by adjusting the distance between the table and the crosshead without using an expensive long-sized screw columns, causing the manufacturing cost of the machine to be reduced.

BRIEF DESCRIPTION OF THE DRAWINGS

In the following is described the present invention in further detail by reference to the accompanying drawings, in which.

DETAILED DESCRIPTION OF THE INVENTION

An embodiment of the present invention is described by reference of FIGS. 1 to 3.

Figure 1:
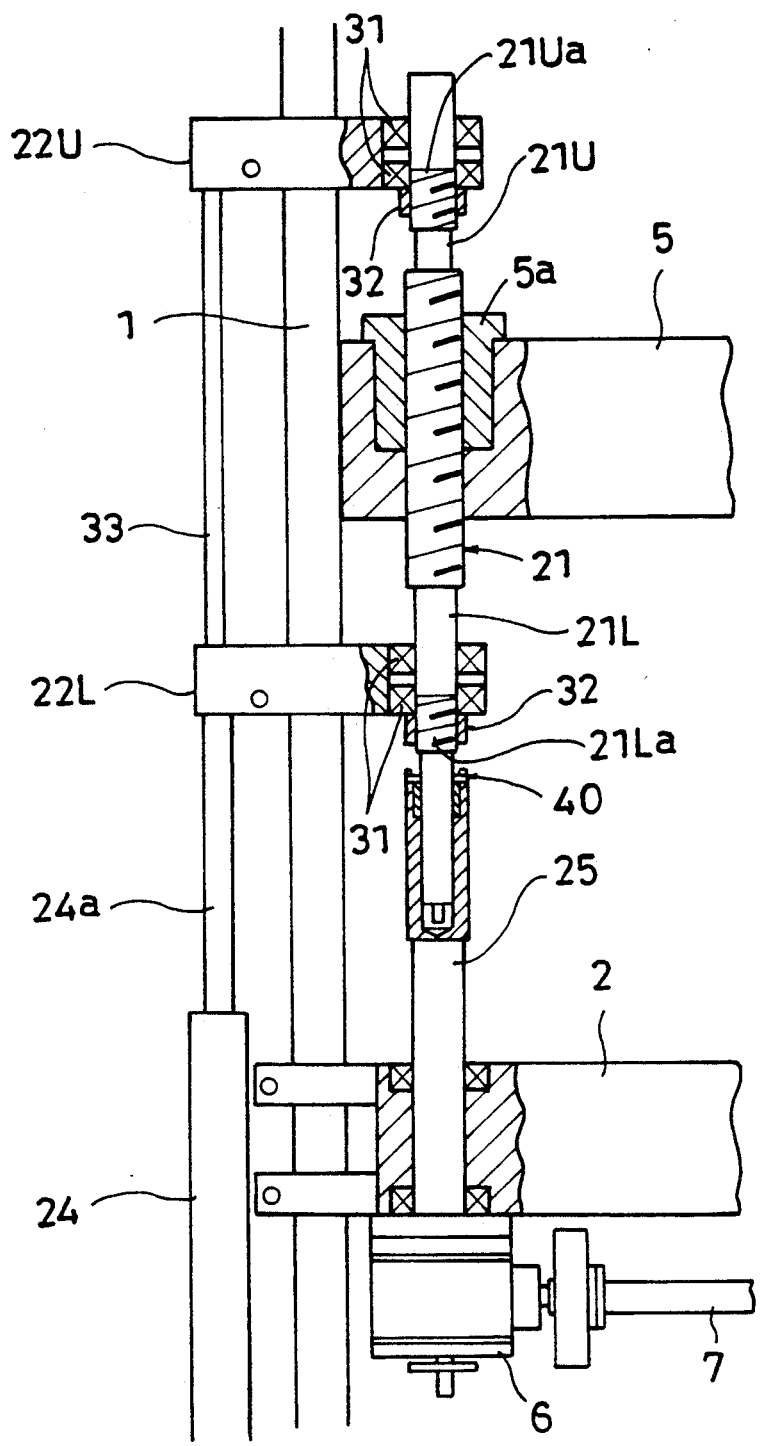
FIG. 1 shows a partial cross section of the principal part of an embodiment of the invented material testing machine having expandable screw columns.
Figure 5:
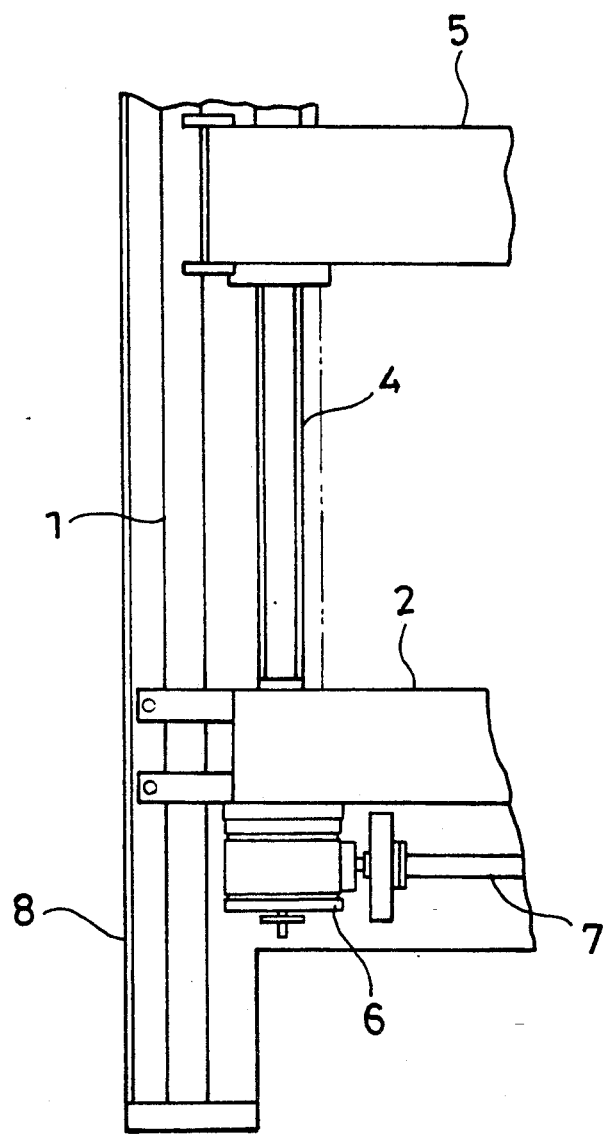
FIG. 5 shows a partially detailed view of the driving mechanism used in the machine shown in FIG. 4.

In FIG. 1, in which an invented material testing machine having expandable screw columns has its left half constitution illustrated as a partially corss-sectional drawing, the parts corresponding to those shown in FIG. 5 are given the same reference numerals with the exception that the screw column shown in FIG. 1 is indicated with a reference numeral 21.

In FIG. 1, a screw column 21 screw-engaged with a nut 5a embedded in a crosshead 5 is threaded in the region corresponding to a stroke given by the crosshead in operation, that is, to a length of elongation of the test piece, and they are rotatably supported by a supporting column 1 through an upper and a lower bearing blocks 22U and 22L.

More concretely, the screw column 21 has its upper and lower shafts 21U and 21L made to rotatably penetrate the bearing blocks 22U and 22L at their end portions with bearings 31 interposed. The screw column 21 is further compressed to the inner races of the bearings 31 with nuts 32 screw-engaged with threaded portions 21Ua and 21La. On the other hand, the bearing blocks 22U and 22L have their other end portions provided, as is shown in FIG. 2, with a split slit 22a, which is penetrated by the supporting column 1. A reference numeral 23 stands for a hydraulic cylinder, which contracts a rods 23a penetrating the bearing block 22U (22L) and makes the same clamped and fixed to the supporting column 1. Further, the upper and lower bearing blocks 22U and 22L are connected with each other through a connecting member 33, with the lower bearing 22L made connected with the rod 24 of a rise-and-fall cylinder 24.

In addition, a speed reduction gear 6 installed on the lower portion of a table 2 is connected with an intermediate rod 25, which rotatably penetrates the table 2 and projects upward. The intermediate rod 25 has its upper end slidably pierced in the axial direction by the tip portion of the lower shaft 21L of the screw column 21 and made capable of being fixed by means of a torque transmission mechanism 40.

Figure 3:
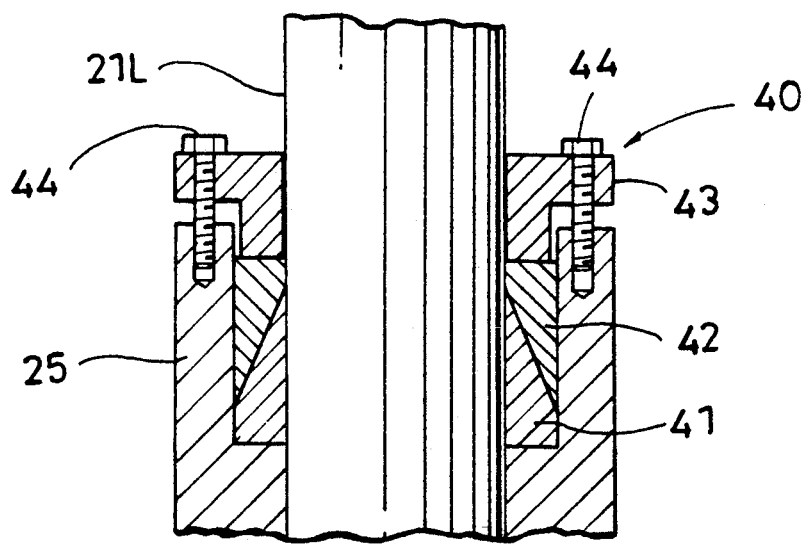
FIG. 3 shows an enlarged view of the torque transmission mechanism used in the present invention.
Figure 4:
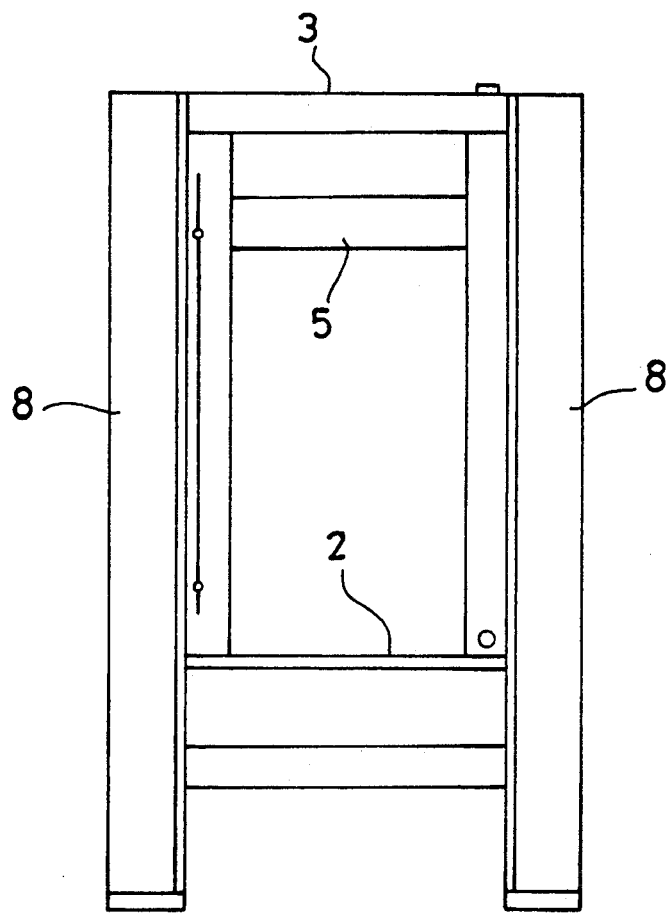
FIG. 4 shows the frontal view of a conventional material testing machine.

The torque transmission mechanism 40, as is illustrated in the enlarged drawing given by FIG. 3, consists of an inner ring 41 slidably put on the shaft 21L, an outer ring 42 put between the inner ring 41 and the intermediate rod 25, and a flange 43 for pressing the outer ring 24. The outer ring 24 is pressed downward by tightening bolts 44 connecting the upper face of the flange 43 to the end surface of the intermediate rod 25.

The outer peripheral surface of the inner ring 41 and the inner peripheral surface of the outer ring 42 are tapered so that the downward pushing of the outer ring 42 causes the outer ring 42 and the inner ring 41 to be pressed, owing to the wedge effect, onto the inner surface of the intermediate rod 25 and the outer surface of the shaft 21L, respectively. Thus the rotation of the intermediate rod 25 is transmitted to the shaft 21L, and therefore, to the screw column 21. On the contrary the loosening of the bolts 44 releases the outer ring 42 from the downward pressing force, enabling the shaft 21L to slide in the axial direction within the intermediate rod 25. Therefore, the torque transmission to the screw column 21 can be adjusted or controlled by varying the tightening force of the bolts 44.

The above description regarding the left half portion of the machine can of course be applied also to the right half which has a construction symmetrically similar to that of the left half.

In the following, the operation of the above embodiment of the present invention is described.

In advance of a tension test on a long test piece, the distance between the table and the crosshead must be adjusted in the following procedure.

Figure 2:
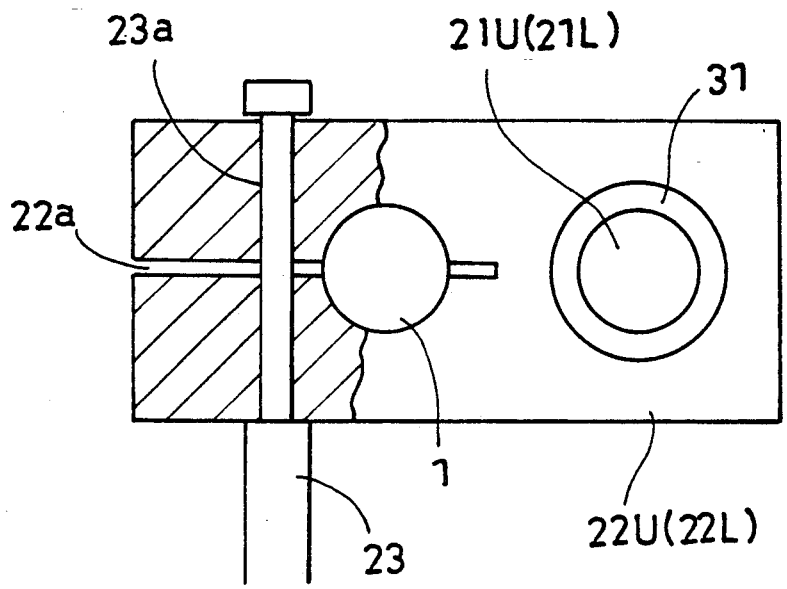
FIG. 2 shows a partially cross-sectional plan view of the bearing block used in the present invention.

First, the lower shaft 21L is made rotatable in the axial direction within the intermediate rod 25 by loosening the bolts 44 of the torque transmission mechanism 40, and the hydraulic cylinder 23 shown in FIG. 2 is extended to make the bearing blocks 22U and 22L release the supporting column 1. With such condition satisfied, the extension of the rod 24a of the rise-and-fall cylinder 24 makes the upper and lower bearing blocks 22U and 22L slide up along the supporting column 1, causing the lower shaft 21L to rise upward, sliding within the intermediate rod 25, together with the screw column 1 and the crosshead 5. In this manner the screw column 1 is expanded with respect to the intermediate rod 25, causing the distance between the table 2 and the crosshead 5 to increase. When the distance is made large in correspondence with the length of the test piece, the rise-and-fall cylinder is stopped.

Next, the shaft 21L is made rotatable in one body with the intermediate rod 25 by tightening the bolts 44 of the torque transmission mechanism 40, and the hydraulic cylinder is contracted to fix the upper and lower bearing blocks 22U and 22L to the supporting column 1. Then the test piece is set between the clutches (not shown) mounted respectively on the table 2 and on the crosshead 5. With the motor driven in a predetermined direction under the above conditions, the intermediate rod 25 is made to rotate through the rotation shaft 7 and the speed reduction gear 6. Thus the crosshead 5 and therefore the upper clutch (not shown) rise upward to exert a tensile force to the test piece. Further, when a test is made on a short sized test piece, the distance between the table 2 and the crosshead 5 is made short by contracting the rise-and-fall cylinder 24 with the lower shaft made slidable in the axial direction within the intermediate rod 25 and with the upper and lower bearing blocks 22U and 22L made slidable along the supporting column 1.

According to the above embodiment, a tension test can be made on a long test piece without using a long-sized screw columns. Particularly in the case of this embodiment, since the rotation of the intermediate rod 25 is transmitted to the screw column 21 by means of a torque transmission mechanism 40 comprising, as shown in FIG. 3, an inner ring 41 and an outer ring 42, the screw column 21 is securely rotated in one body with the intermediate rod 25, making it possible, for instance, to obtain a precision stroke of the crosshead 5 from the number of rotation of the motor or intermediate rod 25.

In the construction of the above embodiment, the table 2 constitutes a base rack, while the bearing blocks 22U and 22L form a holder means.

Further, the torque transmission mechanism 40 can be replaced, for instance, with splines formed on the outer peripheral surface of the shaft 21L and the inner peripheral surface of the intermediate rod 25 so as to be engaged with each other, since such construction also makes the screw column 21 expandable with respect to and rotatable in one body with the intermediate rod 25. According to this construction, however, the backlash in the engaging part of the splines does not always make the rotation of the intermediate rod 25 coincide with that of the screwed column 21, deteriorating the accuracy in deriving the stroke of the crosshead 5 from the rotation of the motor or intermediate rod 25.

Although in the above embodiment the screw column 21 and the crosshead 5 are moved upward or downward by means of the rise-and-fall cylinder 24, the operation of rise-and-fall may be made manually. Further, the holder means are not restricted to the above disclosed construction.

We claim:

1. A material testing machine with screw columns made expandable, said machine comprising:

a pair of rotatable intermediate rods vertically mounted on a base bed so as to be rotated by a motor;

a pair of screw columns provided with screws thereon in a predetermined region corresponding to a possible elongation of a test piece and installed so as to be expandable with respect to and rotatable in one body with said pair of rotatable intermediate rods;

a holder means for rotatably holding said screw columns at any expanded position; and a crosshead for loading a test piece with a test load in cooperation with said base bed, said crosshead having both ends screw-engaged with said pair of screw columns and made movable with respect to said base bed by means of screw rotation.

2. A material testing machine as defined in claim 1, wherein each of said screw columns has its lower tip portion provided with a screwless cylindrical extension; said extension is inserted into an extension receiving hole provided for receiving said extension at the upper end of each of said rotatable intermediate rods; said pair of screw columns is made expandable with respect to and rotatable in one body with said pair of rotatable intermediate rods by inserting into an clearance intentionally provided between said extension and said extension receiveing hole a pair of split type pressing rings formed so as to produce a radial pressing force from a axial pressing force.

3. A material testing machine as defined in claim 1, wherein said holder means for rotatably holding said screw columns at any desired position consists of an upper bearing block and a lower bearing block, each comprising a bearing for supporting the upper or lower part of each of said screw colums and a hydraulic clamping mechanism for a stationary supporting column.

* * * * *